US010786617B2

(12) United States Patent
Niimi et al.

(10) Patent No.: US 10,786,617 B2
(45) Date of Patent: Sep. 29, 2020

(54) BLOOD CIRCULATION SYSTEM

(71) Applicant: SENKO MEDICAL INSTRUMENT Mfg. Co., Ltd., Tokyo (JP)

(72) Inventors: Yoshinari Niimi, Tokyo (JP); Katsunori Tanaka, Tokyo (JP); Masahiro Kihara, Tokyo (JP); Munehiro Kishi, Tokyo (JP); Taku Maruya, Tokyo (JP); Masanori Yoshihara, Tokyo (JP); Masahiro Kamiya, Tokyo (JP)

(73) Assignee: SENKO MEDICAL INSTRUMENT MFG. CO., LTD., Tokyo (JP)

( * ) Notice: Subject to any disclaimer, the term of this patent is extended or adjusted under 35 U.S.C. 154(b) by 423 days.

(21) Appl. No.: 15/503,501

(22) PCT Filed: Aug. 20, 2015

(86) PCT No.: PCT/JP2015/073363
§ 371 (c)(1),
(2) Date: Feb. 13, 2017

(87) PCT Pub. No.: WO2016/027852
PCT Pub. Date: Feb. 25, 2016

(65) Prior Publication Data
US 2017/0232182 A1 Aug. 17, 2017

(30) Foreign Application Priority Data

Aug. 20, 2014 (JP) .................................. 2014-167559
Mar. 17, 2015 (JP) .................................. 2015-053600
Jun. 22, 2015 (JP) .................................. 2015-124810

(51) Int. Cl.
*A61M 1/36* (2006.01)
*A61M 1/10* (2006.01)
*A61M 1/16* (2006.01)

(52) U.S. Cl.
CPC ........ *A61M 1/3666* (2013.01); *A61M 1/1029* (2014.02); *A61M 1/1037* (2013.01);
(Continued)

(58) Field of Classification Search
CPC .............. A61M 1/3666; A61M 1/1029; A61M 1/1039; A61M 1/1603; A61M 1/1629;
(Continued)

(56) References Cited

U.S. PATENT DOCUMENTS 4,598,697 A  7/1986  Numazawa
4,650,457 A  3/1987  Morloka
(Continued)

FOREIGN PATENT DOCUMENTS

CN    102365105 A    2/2012
DE    19622184 A1    12/1997
(Continued)

OTHER PUBLICATIONS

Extended European Search Report for related EP Patent Application No. 15832993.8, dated Jun. 23, 2017, in 7 pages.
(Continued)

*Primary Examiner* — Ariana Zimbouski
(74) *Attorney, Agent, or Firm* — Procopio, Cory, Hargreaves & Savitch LLP

(57) ABSTRACT

The preset invention discloses an artificial heart and lung apparatus (100) including a roller pump (120); a blood removal line (101); a first blood transfer line (104); a blood removal rate sensor (111) and a control unit (140) that performs linked control of the roller pump (120) in correspondence with a blood removal rate. The control unit (140) is capable of detecting that the blood removal rate deviates from a blood removal condition set in advance, and out-of-set condition blood removal is performed.

3 Claims, 10 Drawing Sheets

(52) U.S. Cl.
CPC ........ *A61M 1/1039* (2014.02); *A61M 1/1046* (2013.01); *A61M 1/1086* (2013.01); *A61M 1/1603* (2014.02); *A61M 1/1629* (2014.02); *A61M 1/1698* (2013.01); *A61M 1/3624* (2013.01); *A61M 1/3639* (2013.01); *A61M 1/101* (2013.01); *A61M 1/1006* (2014.02); *A61M 2205/18* (2013.01); *A61M 2205/3303* (2013.01); *A61M 2205/3306* (2013.01); *A61M 2205/3334* (2013.01); *A61M 2205/3365* (2013.01); *A61M 2205/3375* (2013.01); *A61M 2205/50* (2013.01); *A61M 2205/502* (2013.01)

(58) Field of Classification Search
CPC .............. A61M 1/1037; A61M 1/1046; A61M 1/1086; A61M 1/1698; A61M 1/3624; A61M 1/3639
See application file for complete search history.

(56) References Cited

U.S. PATENT DOCUMENTS

| | | | |
|---|---|---|---|
| 5,813,972 | A | 9/1998 | Nazarlan |
| 6,024,692 | A | 2/2000 | Dilling |
| 2010/0042259 | A1 | 2/2010 | Simons |
| 2010/0106101 | A1 | 4/2010 | Fisher et al. |
| 2012/0273415 | A1 | 11/2012 | Gerber |
| 2012/0330214 | A1 | 12/2012 | Peters et al. |
| 2015/0045712 | A1 | 2/2015 | Hiroshima et al. |

FOREIGN PATENT DOCUMENTS

| | | |
|---|---|---|
| EP | 2519282 B1 | 11/2012 |
| EP | 2711037 A1 | 3/2014 |
| GB | 2538577 A | 11/2016 |
| JP | 62-027966 A | 2/1987 |
| JP | 63-143078 A | 6/1988 |
| JP | 2000-000299 A | 1/2000 |
| JP | 2000210381 A | 8/2000 |
| JP | 2000245829 A | 9/2000 |
| JP | 2001-517495 A | 10/2001 |
| JP | 2006-020712 A | 1/2006 |
| JP | 2006043045 A | 2/2006 |
| JP | 2006-325750 A | 12/2006 |
| JP | 2010-517734 A | 5/2010 |
| JP | 2011147710 A | 8/2011 |
| JP | 2013501578 A | 1/2013 |
| JP | 2014046026 A | 3/2014 |
| WO | 80/02376 A1 | 11/1980 |
| WO | 92/02264 A1 | 2/1992 |
| WO | 99/15212 A1 | 4/1999 |
| WO | 2011019655 A2 | 2/2011 |
| WO | 2011/079941 A1 | 7/2011 |
| WO | 2012/141756 A2 | 10/2012 |
| WO | 2013/012776 A1 | 1/2013 |
| WO | 2013/025826 A1 | 2/2013 |
| WO | 2013/128016 A1 | 9/2013 |
| WO | 2013128012 A1 | 9/2013 |
| WO | 2014/121164 A1 | 8/2014 |
| WO | 2015/041150 A1 | 3/2015 |

OTHER PUBLICATIONS

Extended European Search Report for related EP Patent Application No. 15833783.2, dated Jun. 29, 2017, in 8 pages.
Office Action for related U.S. Appl. No. 15/502,949, dated Jun. 29, 2017, in 6 pages.
International Search Report and Written Opinion for PCT App No. PCT/JP2015/073363 dated Nov. 2, 2015, 9 pgs.
International Search Report and Written Opinion for PCT App No. PCT/JP2015/073425 dated Nov. 2, 2015, 9 pgs.
International Search Report and Written Opinion for PCT App No. PCT/JP2015/073428 dated Nov. 2, 2015, 8 pgs.
Communication Pursuant to Article 94(3) EPC for EP App No. 15833783.2 dated Apr. 20, 2018, 5 pgs.
Office Action for JP Patent Application No. 2015-114878, dated Jan. 8, 2019, in 6 pages.
Chinese Office Action dated Dec. 18, 2017 for Chinese Patent Application No. 201580042928.9, 12 pages.
Notice of Reasons for Rejection for related JP App No. 2015-146146 dated Feb. 5, 2019, 6 pgs.
Office Action for related U.S. Appl. No. 15/502,091 dated Apr. 16, 2019, 38 pages.
Notice of Reasons for Rejection for related JP App No. 2015-157773 dated Jul. 23, 2019, 6 pgs.
Office Action for related U.S. Appl. No. 15/502,949 dated Sep. 19, 2019, 7 pages.

BLOOD CIRCULATION SYSTEM

TECHNICAL FIELD

Cross-Reference To Related Applications

The present invention relates to a blood circulation system that circulates removed blood via a blood transfer pump.

This application is a U.S. National Sate entry of PCT application No: PCT/JP2015/073363 filed Aug. 20, 2015, which claims priority to Japanese patent application No. 2014-167559, filed Aug. 20, 2014, Japanese patent application No. 2015-53600, filed Mar. 17, 2015, and Japanese patent application No. 2015-124810, filed Jun. 22, 2015, the contents of which are incorporated herein by reference.

BACKGROUND ART

In the related art, an artificial heart and lung and a blood circulation system for adjunctively circulating blood are widely used as necessary when a heart is stopped or is approximately stopped during or after surgery such as cardiac surgery.

As shown in FIG. 10, an artificial heart and lung apparatus (blood circulation system) 500 equipped with an artificial heart and lung in the related art includes a blood removal line 501; a reservoir 502; a blood line 503; a blood transfer pump 504; a first blood transfer line 505; an artificial lung 506; and a second blood transfer line 507.

The blood removal line 501 transfers blood, which has been received from a vein of a patient (human body) P, to the reservoir 502. The blood removal line 501 is a tube formed of resin such as polyvinyl chloride.

The reservoir 502 includes a tank therein, and temporarily stores the transferred blood.

The blood transfer pump 504 transfers the blood stored in the reservoir 502 to the artificial lung 506 via the blood line 503 through which the reservoir 502 is connected to the blood transfer pump 504, and via the first blood transfer line 505 through which the blood transfer pump 504 is connected to the artificial lung 506. For example, a roller pump or a centrifugal pump is used as the blood transfer pump 504. The blood transfer pump 504 is controlled by a signal output from a blood transfer pump control unit 540.

The artificial lung 506 includes a hollow fiber membrane, a flat membrane, or the like having good gas permeability, and has the function of discharging carbon dioxide from and adding oxygen to blood.

The second blood transfer line 507 receives the blood, from which carbon dioxide has been discharged and to which oxygen has been added by the artificial lung 506, and transfers the blood to an artery of the patient P.

Advanced knowledge and techniques are required to operate the artificial heart and long apparatus 500 with such a configuration. Typically, a clinical engineer adjusts a blood flow rate via a manual operation based on a doctor's instructions.

When adjusting the blood flow rate via a manual operation, the clinical engineer is required to adjust a blood flow rate in the blood removal line 501 by pinching the blood removal line 501 with a forceps while confirming the degree of removal of blood or an arterial pressure of the patient.

Since the clinical engineer adjusts the amount of discharge of the blood transfer pump by manually controlling the rotational speed of the blood transfer pump (a roller pump, a centrifugal pump, or the like) when adjusting the blood flow rate, a complex and advanced operation technique is required in addition to the adjustment of each line.

Patent Document 1 discloses technology to adjust a blood removal rate in which the blood removal line 501 is pinched and deformed to accurately and simply adjust the blood removal rate via an artificial heart and lung apparatus.

In order to adjust the flow rate of blood to be removed via the blood removal line 501, the artificial heart and lung apparatus disclosed in Patent Document 1 pinches and deforms the blood removal line 501 by operating a blood removal regulator 521, which includes a clamper formed of a pair of clamp members and a servo motor, via a blood removal regulator operation unit 520.

In contrast, in a surgery using a blood circulation system, a suitable balance between the transfer of blood and the removal of blood is required. If a possibility that a blood removal rate may change depending on surgical situations is taken into consideration, desirably, blood is smoothly and stably circulated even if the blood removal rate may change.

Patent Document 2 discloses technology in which a blood removal regulator control unit is linked with a blood transfer regulator control unit, a blood removal rate and a blood transfer rate are simultaneously controlled via operation of one of the control units, and thus a blood flow rate of an artificial heart and lung apparatus is efficiently adjusted.

CITATION LIST

Patent Document

[Patent Document 1] Japanese Unexamined Patent Application, First Publication No. 62-027966

[Patent Document 2] Japanese Unexamined Patent Application, First Publication No. 2006-020712

SUMMARY OF INVENTION

Technical Problem

In contrast, if the blood transfer rate is increased in correspondence with a change in the blood removal rate during surgery, even if a balance between the blood transfer rate and the blood removal rate is struck, there is a possibility that blood pressure and blood transfer pressure may excessively increase.

If a blood level of a reservoir decreases due to a decrease in the blood removal rate, there is a need of paying attention to the undesirable transfer of air.

The present invention is made in light of this problem, and an object of the present invention is to provide a blood circulation system that is capable of efficiently circulating blood to smoothly and stably proceed with surgery even if the blood removal rate changes.

Solution to Problem

In order to solve this problem, the invention proposes the following means.

According to a first aspect of the present invention, there is provided a blood circulation system that can be connected to a human body, and transfers removed blood to the human body via a blood transfer pump, the system including: the blood transfer pump; a blood removal line through which removed blood flows to the blood transfer pump; a blood transfer line that transfers blood, which is sent from the blood transfer pump, to the human body; blood removal rate measurement means that is provided in the blood removal line and measures a blood removal rate; and a control unit that controls a blood transfer rate of the blood transfer pump. The control unit is configured to be capable of detecting that the blood removal rate has deviated from a blood removal condition set in advance, and out-of-set condition blood removal is performed.

Since the control unit is capable of detecting that the blood removal rate deviates from the blood removal condition set in advance, and the out-of-set condition blood removal is performed, the blood circulation system of the invention is capable of efficiently detecting an occurrence of the out-of-set condition blood removal in a short period of time.

As a result, even if the blood removal rate changes, it is possible to smoothly and stably perform surgery.

In the present invention, the blood removal condition represents an upper limit value of a blood removal rate, a lower limit value of the blood removal rate, the range of the blood removal rate defined by the upper and lower limit values of the blood removal rate, and the range (including a range specified by a ratio of the blood transfer rate to the reference blood removal rate or a flow rate difference therebetween, and a blood transfer rate equal to or higher than the reference blood removal rate, or equal to or lower than the reference blood removal rate) of a reference blood removal rate set in advance. The range to specify the blood removal condition or the reference blood removal rate may change together with parameters such as time.

The blood removal condition may include a plurality of blood removal rates corresponding to a plurality of conditions.

In the present invention, the blood removal line is a blood line among blood lines of the blood circulation system, which is formed such that blood removed from the human body flows through the blood line toward the blood transfer pump. More specifically, a blood line leading toward to a reservoir or the like is a blood line which is positioned on the upstream side of a portion (for example, a reservoir) in which blood is released to a space, and in which there is normally no continuity of a blood flow rate.

The blood transfer line is a blood line leading toward a human body side from the blood transfer pump.

For the sake of convenience, in a blood circulation path, configuration elements that are not the blood removal line or the blood transfer line, or a line indicating a portion of the blood transfer line or the blood removal line may be referred to as blood lines.

In the present invention, the blood removal rate measurement means includes not only measurement means for measuring a blood removal rate, but also measurement means for measuring various blood removal rate parameters to specify a blood removal rate.

The blood removal rate parameters are parameters that change in correspondence with the blood removal rate, and also include the blood removal rate. In contrast, the blood removal rate parameters include various parameters to specify a blood removal rate such as the flow speed of removed blood in a case where a cross-sectional flow path area of the blood removal line is already known, or a parameter (for example, a change in ultrasonic wave frequency) to specify the flow speed.

In a second aspect of the present invention according to the first aspect, if the out-of-set condition blood removal is detected, the control unit outputs an alarm.

Since, if the out-of-set condition blood removal is detected, the control unit outputs alarm, the blood circulation system of the invention is capable of efficiently recognizing a change in blood removal rate.

In a third aspect of the present invention according to the first or second aspect, the control unit is capable of performing linked control of the blood transfer pump in correspondence with the blood removal rate such that the blood transfer rate of the blood transfer pump is in a specific range of the blood removal rate measured by the blood removal rate measurement means, and when the linked control is performed, if it is detected that the blood removal rate has exceeded a set upper limit blood removal rate, that is, if the out-of-set condition blood removal is detected, the control unit performs control such that the blood transfer rate of the blood transfer pump is limited to an upper limit value of the blood transfer rate or less while being independent of the blood removal rate.

If, when the blood transfer rate is controlled according to the blood removal rate, the out-of-set condition blood removal is detected, that is, it is detected that the blood removal rate has exceeded the set upper limit blood removal rate, the blood circulation system of the invention is capable of performing control such that the blood transfer rate of the blood transfer pump becomes the upper limit value of the blood transfer rate or less.

Accordingly, even if the blood removal rate changes and increases, the blood transfer rate is limited to the upper limit value of the blood transfer rate. As a result, it is possible to prevent an increase in blood pressure and blood transfer pressure, and to smoothly and stably perform surgery.

In the present invention, the linked control implies that the blood transfer rate of the blood transfer pump is controlled according to the blood removal rate, and implies that the blood transfer rate of the blood transfer pump is controlled to be in the specific range of the blood removal rate.

The feet that the blood transfer rate is in the specific range of the blood removal rate implies that the blood transfer rate is in the condition range that is set for the blood removal rate in advance. A determination as to whether the blood transfer rate is in the specific range of the blood removal rate can be made by a flow rate difference (for example, an upper limit flow rate difference or a lower limit flow rate difference) between the blood transfer rate and the blood removal rate or a ratio therebetween. The fact that the blood transfer rate is in the specific range of the blood removal rate includes a case in which the blood transfer rate is synchronized with the blood removal rate.

The synchronization of the blood transfer rate with the blood removal rate implies that the blood transfer rate of the blood transfer pump is set to be equal to the blood removal rate, and includes a case in which the blood transfer rate exactly coincides with the blood removal rate, and a case in which the blood transfer rate substantially coincides with the blood removal rate. For example, errors caused by a time lag of a control signal output to the blood transfer pump or a response time of the blood transfer pump are allowed.

The synchronization includes a case in which the same blood flow rate as the blood removal rate is transferred by the blood transfer pump after a delay time set in advance.

The fact that the blood transfer rate of the blood transfer pump is in the specific range of the blood removal rate measured by the blood removal rate measurement means includes a case in which the blood transfer rate is controlled to be in the specific range by direct controlling of the blood transfer pump based on measured values of the blood removal rate parameters, instead of calculating the blood removal rate.

In the present invention, the normal control implies that the blood transfer rate of the blood transfer pump is controlled independent of the blood removal rate, and implies that the blood transfer rate is not controlled according to the blood removal rate. The normal control includes control that is performed based on an instruction regarding a blood transfer rate which is given by a manual operation, and control that is performed based on conditions set in advance.

In a fourth aspect of the present invention according to the first to third aspects, the blood circulation system further includes flow rate adjustment means for adjusting the flow rate of blood flowing through at least one of the blood removal line and the blood transfer line. The control unit is capable of performing the linked control such that the blood transfer rate of the blood transfer pump is in the specific range of the blood removal rate measured by the blood removal rate measurement means, and if the out-of-set condition blood removal is detected, the control unit adjusts the blood flow rate via the blood removal rate adjustment means.

The blood circulation system of the invention includes the flow rate adjustment means for adjusting the flow rate of blood flowing through at least one of the blood removal line and the blood transfer line. If the out-of-set condition blood removal is detected in the linked control, the control unit adjusts the blood flow rate via the blood removal rate adjustment means. As a result, the blood circulation system is capable of efficiently adjusting the flow rate of blood flowing through the blood removal line or the blood transfer line.

In a fifth aspect of the present invention according to the third or fourth aspect, the control unit controls the blood transfer rate of the blood transfer pump independent of the blood removal rate, and if the out-of-set condition blood removal is deactivated, the control unit returns blood transfer via the blood transfer pump to the linked control.

The control unit performs an out-of-set condition blood removal process in the normal control in which the blood transfer rate of the blood transfer pump is controlled independent of the blood removal rate, and if the out-of-set condition blood removal is deactivated, the control unit returns blood transfer via the blood transfer pump to the linked control. As a result, the blood circulation system of the invention is capable of efficiently performing the linked control.

Advantageous Effects of Invention

Since the control unit is capable of detecting that the blood removal rate deviates from the blood removal condition set in advance, and the out-of-set condition blood removal is performed, the blood circulation system of the invention is capable of efficiently detecting an occurrence of the out-of-set condition blood removal in a short period of time.

As a result, even if the blood removal rate changes, it is possible to smoothly and stably perform surgery.

DESCRIPTION OF EMBODIMENTS

First Embodiment

Hereinafter, an artificial heart and lung apparatus (blood circulation system) of a first embodiment of the present invention will be described with reference to FIGS. 1 to 5.

Figure 1:
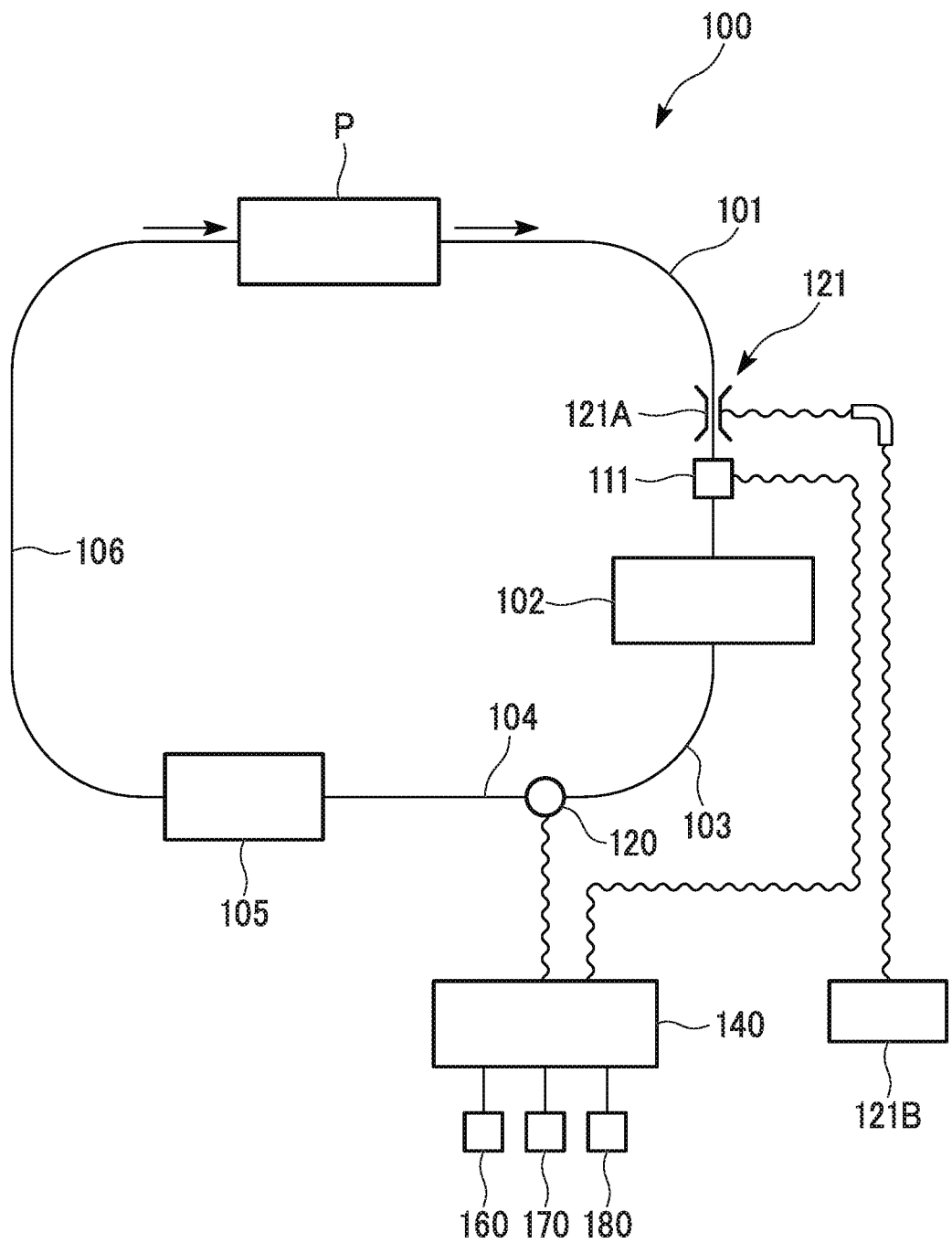
FIG. 1 is a circuit diagram showing a schematic configuration of an artificial heart and lung apparatus of a first embodiment of the present invention.
Figure 2:
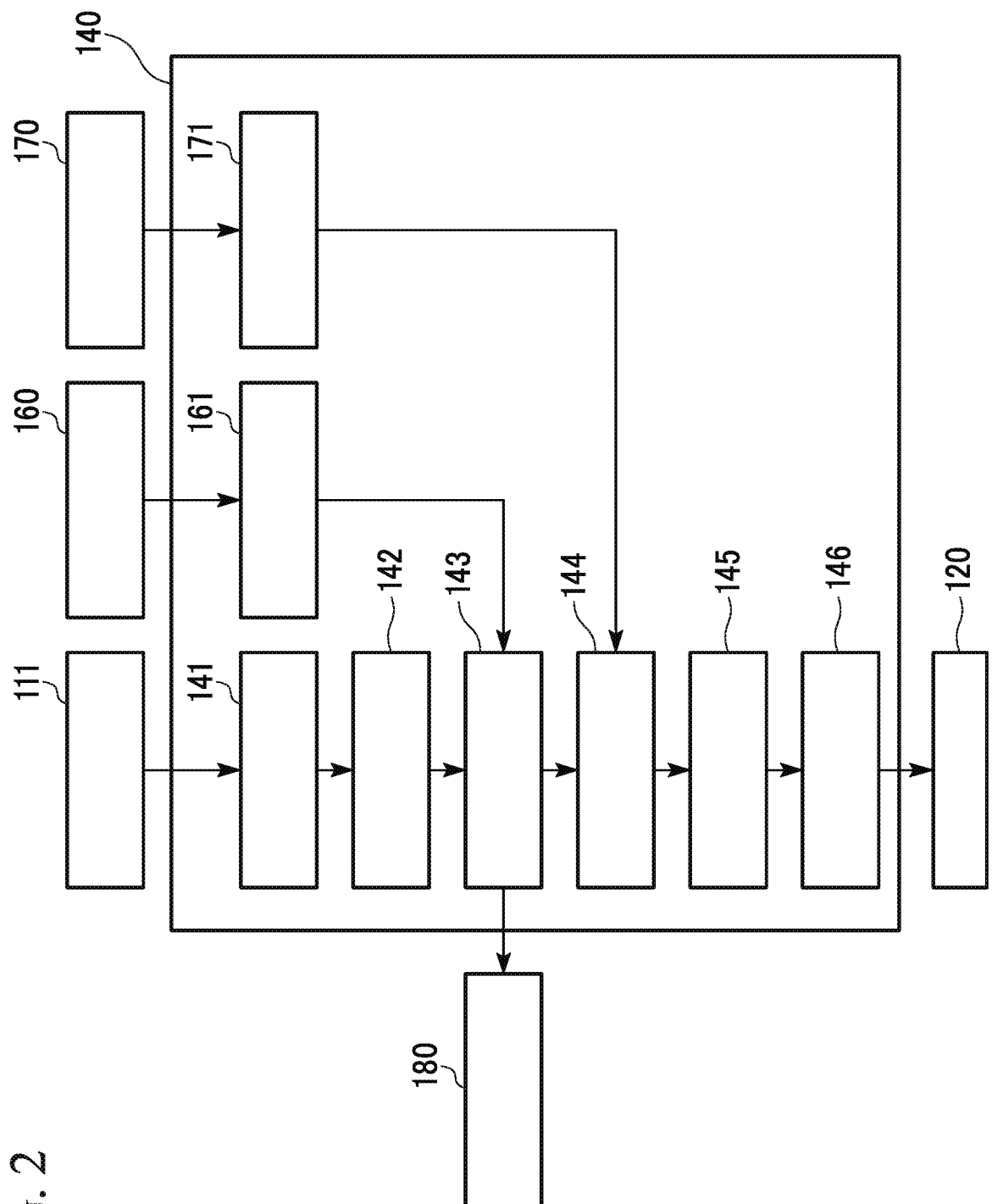
FIG. 2 is a block diagram showing a schematic configuration of a control unit of the artificial heart and lung apparatus of the first embodiment of the present invention.

FIG. 1 is a circuit diagram showing a schematic configuration of the artificial heart and lung apparatus of the first embodiment of the present invention. FIG. 2 is a block diagram showing a schematic configuration of a control unit of the artificial heart and lung apparatus of the first embodiment.

In FIGS. 1 and 2, reference sign 100 represents an artificial heart and lung apparatus, reference sign 111 represents a blood removal rate sensor (blood removal rate measurement means), reference sign 120 represents a roller pump, reference sign 140 represents a control unit, reference sign 160 represents a blood removal condition setting unit, reference sign 170 represents a blood transfer control switching unit, and reference sign 180 represents an out-of-condition blood removal display unit.

As shown in FIG. 1, the artificial heart and lung apparatus 100 includes a blood removal line 101; a reservoir 102; a blood line 103; a first blood transfer line (blood transfer line) 104; an artificial lung 105; a second blood transfer line (blood transfer line) 106; a blood removal rate sensor 111; a blood removal regulator (blood removal rate adjustment means) 121; a roller pump (blood transfer pump) 120; a control unit 140; a blood removal condition setting unit 160; a blood transfer control switching unit 170; and an out-of-condition blood removal display unit 180.

In the embodiment, the artificial heart and lung apparatus 100 is capable of performing control in two ways, that is, the performing normal control in which a blood transfer rate of the roller pump 120 is set independent of a blood removal rate, and the linked control in which the blood transfer rate is set according to the blood removal rate.

If out-of-set condition blood removal (representing a state in which a blood removal rate exceeds a set upper limit blood removal rate, or a state in which a blood removal rate is lower than a set lower limit blood removal rate, and hereinafter, referred to as out-of-condition blood removal) is performed in the normal control, the out-of-condition blood removal display unit 180 is turned on.

If out-of-condition blood removal is performed in the linked control, the out-of-condition blood removal display unit 180 is turned on, and if a blood removal rate exceeds the set upper limit blood removal rate during the out-of-condition blood removal, blood is transferred at an upper limit value of the blood transfer rate.

The blood removal line 101, the reservoir 102, the blood line 103, the roller pump 120, the first blood transfer line 104, the artificial lung 105, and the second blood transfer line 106 are connected together in the listed sequence.

The blood removal regulator 121 and the blood removal rate sensor 111 are disposed in the blood removal line 101 in the listed sequence.

Blood to be removed via the blood removal line 101 is circulated to a patient (human body) P via the first blood transfer line 104 and the second blood transfer line 106.

The blood removal line 101 is a tube formed of resin such as polyvinyl chloride. One end of the blood removal line 101 can be connected to the patient P, and transfers blood, which has been received from a vein, to the reservoir 102.

A sensor or the like (not shown) is provided in the blood removal line 101 so as to monitor the concentration of blood or the concentration of oxygen as necessary. The sensor or the like may be provided in the blood line 103 or the first blood transfer line 104 instead of the blood removal line 101.

The reservoir 102 includes a tank therein, and temporarily stores the transferred blood.

A suction line (not shown) is connected to the reservoir 102 so as to suction blood in a surgical site of the patient P, and a vent line (not shown) is connected to the reservoir 102 so as to suction blood in a right cardiac chamber.

The blood line 103 has the same configuration as that of the blood removal line 101. The upstream side of the blood line 103 is connected to the reservoir 102, and the downstream side of the blood line 103 is connected to the roller pump 120. The blood line 103 transfers the blood, which has been received from the reservoir 102, to the roller pump 120.

The roller pump 120 includes a rotating roller and a tube that is disposed on the outside of the rotating roller and is formed of flexible resin. If the rotating roller rotates, the tube passes through the rotating roller, and blood is suctioned and transferred out, the blood stored in the reservoir 102 is suctioned via the blood line 103, and is transferred to the artificial lung 105 via the first blood transfer line 104.

The rotational speed of the rotating roller is controlled by a rotation control signal output from the control unit 140, and the roller pump 120 suctions and transfers an amount of blood corresponding to the rotational speed of the rotating roller.

The first blood transfer line 104 has the same configuration as that of the blood removal line 101. The upstream side of the first blood transfer line 104 is connected to the roller pump 120, and the downstream side of the first blood transfer line 104 is connected to the artificial lung 105. The first blood transfer line 104 transfers the blood, which has been transferred out from the roller pump 120, to the artificial lung 105.

The artificial lung 105 includes a hollow fiber membrane, a flat membrane, or the like having good gas permeability, and discharges carbon dioxide from and adds oxygen to blood.

A heat exchanger is formed integrally with the artificial lung 105 so as to adjust the temperature of blood.

The second blood transfer line 106 has the same configuration as that of the blood removal line 101, and receives the blood, from which carbon dioxide has been discharged and to which oxygen has been added, from the artificial lung 105, and transfers the blood to an artery of the patient P.

A filter (not shown) is provided in the second blood transfer line 106 so as to remove foreign matter such as thrombi and bubbles from blood.

The blood removal regulator 121 is provided in the blood removal line 101. The blood removal regulator 121 includes a clamper 121A formed of a pair of clamp members; a servo motor (not shown) that operates the clamper 121A; and a blood removal regulator operation unit 121B. An operator changes the cross-sectional area of the blood removal line 101 by adjusting the amount of clamp (the amount of pinch) of the clamper 121A via the servo motor driven by manually operating the blood removal regulator operation unit 121B, and as a result, the removal rate of blood flowing through the blood removal line 101 is adjusted.

Quantitative characteristics of a cross-sectional flow path area of the blood removal line 101 with respect to the amount of clamp of the clamper 121A are known. An operator can gradually increase or decrease a blood removal rate by changing the amount of clamp, that is, by linearly changing the cross-sectional flow path area or changing the amount of clamp based on a predetermined function (curve or the like).

The blood removal rate sensor (blood removal rate measurement means) 111 is provided in the blood removal line 101. An ultrasonic sensor that measures the flow speed of blood via ultrasonic waves is used as the blood removal rate sensor 111. The blood removal rate sensor 111 transmits a blood removal rate signal (blood removal rate parameter signal) to the control unit 140.

Hereinafter, a schematic configuration of the control unit 140 will be described with reference to FIG. 2. FIG. 2 is a block diagram showing the schematic configuration of the control unit 140 of the first embodiment.

The control unit 140 includes a blood removal rate signal input receiving unit 141; a blood removal rate calculation unit 142; an out-of-condition blood removal process unit 143; a blood transfer rate calculation unit 144; a roller pump control amount calculation unit 145; a roller pump control unit 146: a set blood removal condition data receiving unit 161; and a blood transfer control switching instruction receiving unit 171.

The control unit 140 is connected to the blood removal rate sensor 111, the roller pump 120, the blood removal condition setting unit 160, the blood transfer control switching unit 170, and the out-of-condition blood removal display unit 180 via cables.

An operator is capable of setting set blood removal condition data which is suitable for proceeding with surgery via the blood removal condition setting unit 160, based on attributes (physical features including a body weight and the like) of the patient P and type of the surgery.

The set blood removal condition data includes out-of-condition blood removal determination data and out-of-condition blood removal process data.

The out-of-condition blood removal determination data includes a set upper limit blood removal rate, a set lower limit blood removal rate, and the like. The out-of-condition blood removal process data includes an upper limit value of the blood transfer rate.

The blood transfer control switching unit 170 is configured to instruct the artificial heart and lung apparatus 100 to transfer blood in either the normal control or the linked control. The blood transfer control switching unit 170 includes an alternative switch.

The blood transfer control switching unit 170 may include a plurality of configuration elements such as a sensor which instructs the artificial heart and lung apparatus 100 to transition to the normal control.

The out-of-condition blood removal display unit 180 is formed of LED lamps or the like. If a blood removal rate is a flow rate of the out-of-condition blood removal, the out-of-condition blood removal display unit 180 is turned on by an output from the out-of-condition blood removal process unit 143, and displays an out-of-condition blood removal state.

The set blood removal condition data receiving unit 161 receives set blood removal condition data from the blood removal condition setting unit 160.

The blood transfer control switching instruction receiving unit 171 receives a blood transfer control switching instruction from the blood transfer control switching unit 170.

The blood removal rate signal input receiving unit 141 is connected to the blood removal rate sensor 111, and receives a blood removal rate signal (blood removal rate parameter signal) sent from the blood removal rate sensor 111.

The blood removal rate calculation unit 142 calculates a blood removal rate based on the blood removal rate signal sent from the blood removal rate signal input receiving unit 141. Specifically, the blood removal rate calculation unit 142 calculates a blood removal rate by multiplying a blood removal speed (flow rate parameter), which is calculated from the blood removal rate signal, by a flow path area of the blood removal line 101.

The out-of-condition blood removal process unit 143 determines whether the blood removal rate is in a blood removal condition range, and detects out-of-condition blood removal, based on the blood removal rate received from the blood removal rate calculation unit 142 and the set blood removal condition data received from the set blood removal condition data receiving unit 161. If the out-of-condition blood removal is performed, the out-of-condition blood removal process unit 143 turns the out-of-condition blood removal display unit 180 on.

If the blood removal rate is in the blood removal condition range, and the blood removal rate of the out-of-condition blood removal does not exceed the set upper limit blood removal rate, that is, if (blood removal rate≤set upper limit blood removal rate) is satisfied, the out-of-condition blood removal process unit 143 sends the blood removal rate, which has been received from the blood removal rate calculation unit 142, to the blood transfer rate calculation unit 144.

In contrast, if the out-of-condition blood removal is performed, and the blood removal rate exceeds the set upper limit blood removal rate, that is, if (blood removal rate>set upper limit blood removal rate) is satisfied, the out-of-condition blood removal process unit 143 sets and sends an upper limit value of the blood transfer rate to the blood transfer rate calculation unit 144.

The set blood removal condition data, which the out-of-condition blood removal process unit 143 has received from the set blood removal condition data receiving unit 161, includes the set upper limit blood removal rate, the set lower limit blood removal rate, and the upper limit value of the blood transfer rate.

The set upper limit blood removal rate is provided to prevent patient's blood pressure of blood transferred via the linked control and blood transfer pressure from excessively increasing in a case where the blood removal rate exceeds the set upper limit blood removal rate.

The set upper limit blood removal rate and the upper limit value of the blood transfer rate may not necessarily be fixed numerical values, and may be changing numerical values defined by a function or the like which takes into consideration blood pressure, relationships between blood transfer pressure and the set upper limit blood removal rate and the upper limit value of the blood transfer rate, and relationships between a successive surgical time and the set upper limit blood removal rate and the upper limit value of the blood transfer rate.

The blood transfer control switching unit 160 is capable of switching between the normal control and the linked control, and the blood transfer rate calculation unit 144 calculates blood transfer rates (target blood transfer rate) of the roller pump 120 in the normal control and the linked control.

The blood transfer rate calculation unit 144 calculates the blood transfer rate of the normal control based on the amount of operation of a blood transfer rate adjustment latch (not shown) which has been received via the out-of-condition blood removal process unit 143.

The blood transfer rate calculation unit 144 calculates a normal (is not the out-of-condition blood removal) blood transfer rate of the linked control based on the blood removal rate received via the out-of-condition blood removal process unit 143.

In the embodiment, the blood transfer rate is synchronized with the blood removal rate by making a blood transfer rate (target blood transfer rate) of the roller pump 120 equal to the blood removal rate.

The synchronization of the blood transfer rate with the blood removal rate via the roller pump 120 is one mode in which the blood transfer rate is controlled to be in a specific range (for example, in a range represented by a ratio of the blood transfer rate to the blood removal rate, or in a range represented by a flow rate difference between the blood transfer rate and the blood removal rate) of the blood removal rate.

The blood transfer rate calculation unit 144 calculates a blood transfer rate of the linked control in a case where (blood removal rate>set upper limit blood removal rate) is satisfied, based on the upper limit value of the blood transfer rate received from the out-of-condition blood removal process unit 143.

In the embodiment, if (blood removal rate≤set upper limit blood removal rate) is satisfied after the blood transfer rate is calculated based on the upper limit value, an out-of-condition blood removal process is deactivated, and the blood transfer rate calculation unit 144 automatically returns to the calculation of a normal blood transfer rate of the linked control.

The roller pump control amount calculation unit 145 calculate rotational speeds (control amounts) of the normal control and the linked control which are output to the roller pump 120, based on the blood transfer rates sent from the blood transfer rate calculation unit 144.

The rotational speeds of the roller pump 120 are calculated by referring to a data table representing a relationship between the rotational speed and the blood transfer rate of the roller pump 120 which represents a blood transfer rate characteristic of the roller pump 120, or by computing a calculation expression representing the relationship between the rotational speed and the blood transfer rate of the roller pump 120.

The rotational speed of the roller pump 120 that is set for the linked control is a rotational speed for synchronizing the blood transfer rate of the roller pump 120 with the blood removal rate.

The roller pump control unit 146 outputs a signal to the roller pump 120 in correspondence with the control amount received from the roller pump control amount calculation unit 145.

<Switching Between Normal Control and Linked Control>

Figure 3:
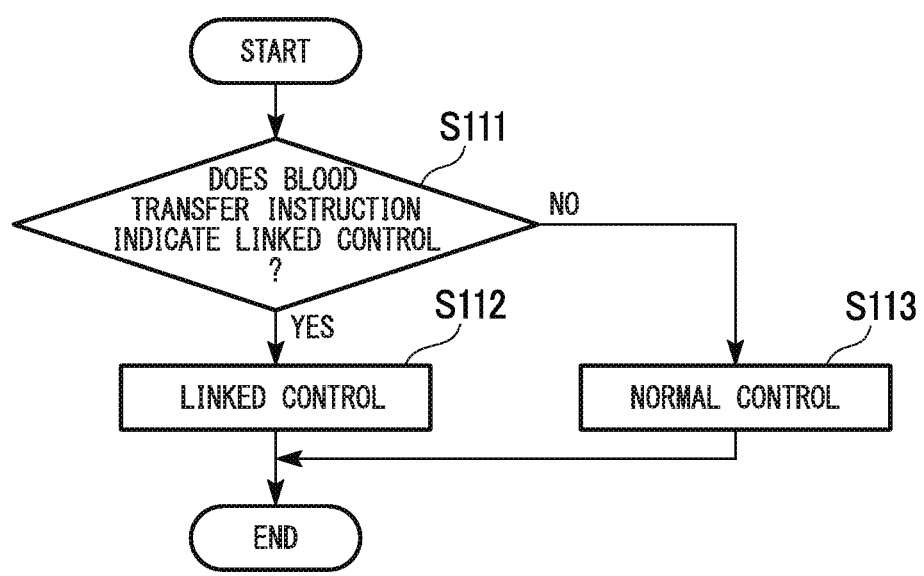
FIG. 3 is a flowchart showing switching between normal control and linked control of the artificial heart and long apparatus of the first embodiment of the present invention.

Hereinafter, switching between the normal control and the linked control of the artificial heart and lung apparatus 100 of the first embodiment will be described with reference to FIG. 3. FIG. 3 is a flowchart showing switching between the normal control and the linked control of the artificial heart and lung apparatus 100.

The switching between the normal control and the linked control of the artificial heart and lung apparatus 100 is performed in the following sequence.

First the blood transfer control switching unit 170 determines whether a blood transfer control switching instruction indicates the linked control (S111).

If the blood transfer control switching instruction indicates the linked control (S111: Yes), the process proceeds to a step in which the linked control of the artificial heart and lung apparatus 100 is performed (S112). If the blood transfer control switching instruction does not indicate the linked control (indicates the normal control) (S111: No), the process proceeds to a step in which the normal control of the artificial heart and lung apparatus 100 is performed (S113).

S111 to S113 are repeatedly executed at predetermined intervals while the artificial heart and lung apparatus 100 is in operation.

<Normal Control>

Figure 4:
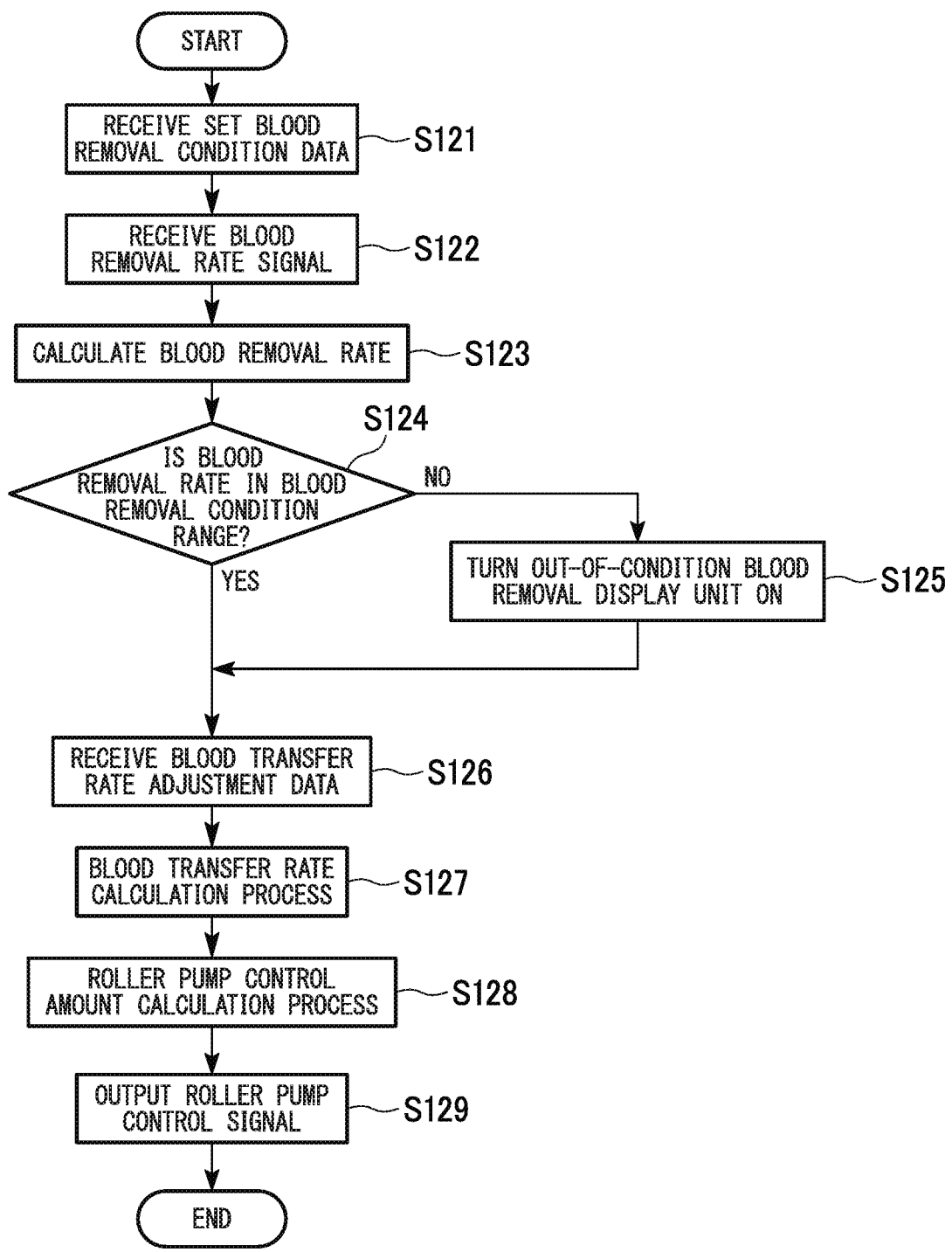
FIG. 4 is a flowchart showing an example of an operational sequence in the normal control of the artificial heart and lung apparatus of the first embodiment of the present invention.

Hereinafter, an example of an operational sequence, in a case where a blood transfer rate of the normal control is adjusted by operating a blood transfer rate adjustment unit (not shown) of the artificial heart and lung apparatus 100, will be described with reference to FIG. 4. FIG. 4 is a flowchart showing an example of an operational sequence of the normal control of the artificial heart and lung apparatus 100.

The operational sequence of the normal control of the artificial heart and lung apparatus 100 is as follows.

(1) First, the set blood removal condition data receiving unit 161 receives set blood removal condition data input from the blood removal condition setting unit 160 (S121).

(2) Subsequently, the blood removal rate signal input receiving unit 141 receives a blood removal rate signal (blood removal rate parameter signal) (S122).

(3) Subsequently, the blood removal rate calculation unit 142 calculates a blood removal rate based on the received blood removal rate signal (S123).

(4) Subsequently, the out-of-condition blood removal process unit 143 determines whether the blood removal rate is in the blood removal condition range by comparison of the blood removal rate calculated in S123 with the blood removal condition data (for example, the set upper limit blood removal rate and the set lower limit blood removal rate) (S124).

A determination as to whether the blood removal rate is in the blood removal condition range is made based on whether the blood removal rate satisfies (set upper limit blood removal rate≥blood removal rate≥set lower limit blood removal rate).

If the blood removal rate is not in the blood removal condition range (S124: No), the out-of-condition blood removal display unit 180 is turned on, and the process proceeds to a step in which the out-of condition blood removal display unit 180 displays an out-of-condition blood removal state (S125). If the blood removal rate is in the blood removal condition range (S124: Yes), the process proceeds to a step in which the blood transfer rate calculation unit 144 receives blood transfer rate adjustment data input from the blood transfer rate adjustment unit (not shown) (S126).

(5) Subsequently, the blood transfer rate calculation unit 144 calculates a blood transfer rate based on the received blood transfer rate adjustment data (S127).

(6) Subsequently, the roller pump control amount calculation unit 145 calculates a control amount (rotational speed) with reference to the blood transfer rate characteristic of the roller pump 120, based on the blood transfer rate calculated in S127 (S128).

(7) Subsequently, the roller pump control unit 146 outputs a signal to the roller pump 120 in correspondence with the control amount (S129).

S121 to S129 are repeatedly executed at predetermined intervals while the normal control of the artificial heart and lung apparatus 100 is performed.

<Linked Control>

Figure 5:
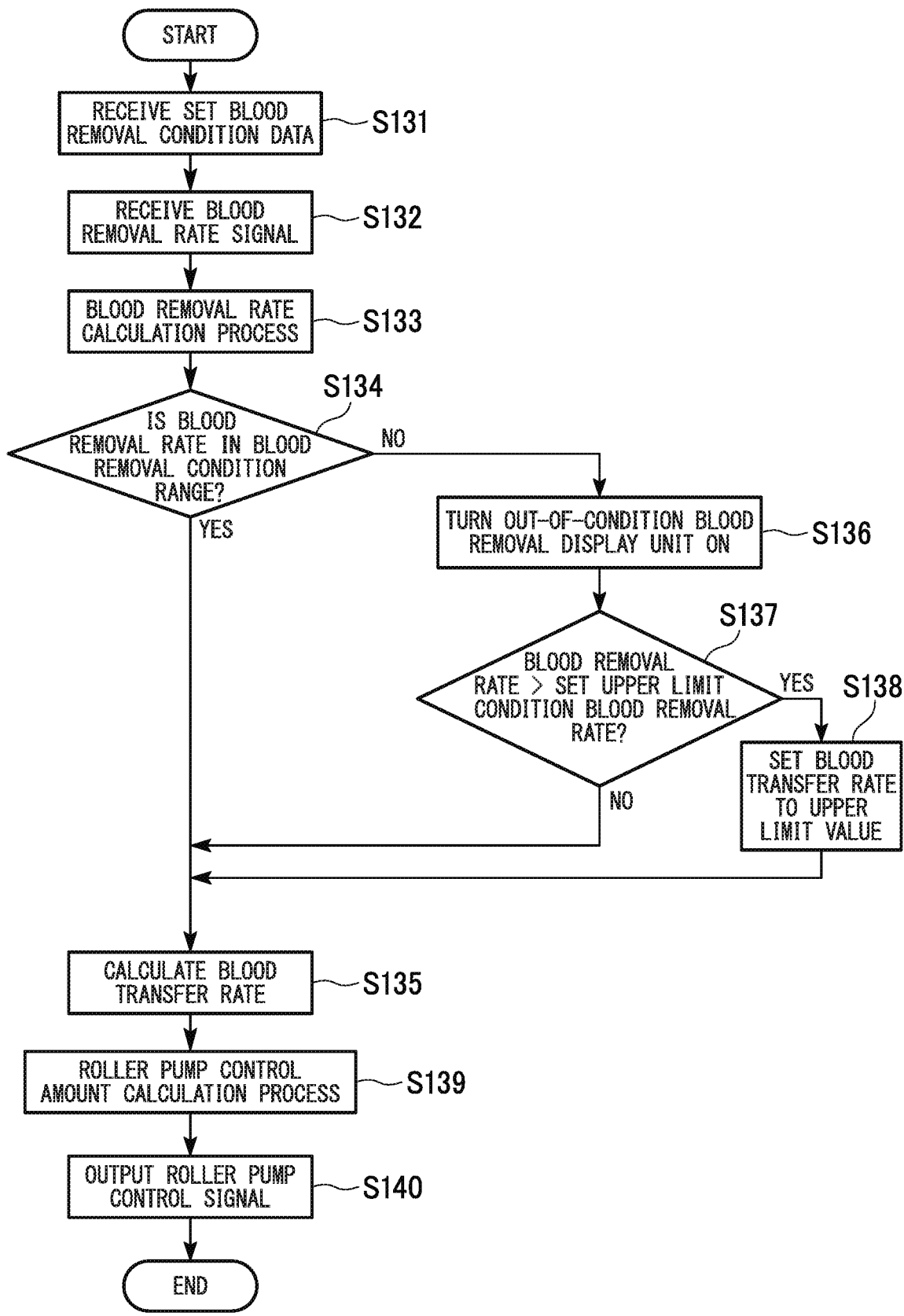
FIG. 5 is a flowchart showing an example of an operational sequence in the linked control of the artificial heart and lung apparatus of the first embodiment of the present invention.

Hereinafter, an example of an operational sequence of the linked control of the artificial heart and lung apparatus 100 will be described with reference to FIG. 5. FIG. 5 is a flowchart showing an example of an operational sequence of the linked control of the artificial heart and lung apparatus 100.

The operational sequence of the linked control of the artificial heart and lung apparatus 100 is as follows.

(1) First, the set blood removal condition data receiving unit 161 receives set blood removal condition data input from the blood removal condition setting unit 160 (S131).

(2) Subsequently, the blood removal rate signal input receiving unit 141 receives a blood removal rate signal (blood removal rate parameter signal) (S132).

(3) Subsequently, the blood removal rate calculation unit 142 calculates a blood removal rate based on the received blood removal rate signal (S133).

(4) Subsequently, the out-of-condition blood removal process unit 143 determines whether the blood removal rate is in the blood removal condition range by comparison of the blood removal rate calculated in S133 with the blood removal condition data (for example, the set upper limit blood removal rate and the set lower limit blood removal rate) (S134).

A determination as to whether the blood removal rate is in the blood removal condition range is made based on whether the blood removal rate satisfies (set upper limit blood removal rate≥blood removal rate≥set lower limit blood removal rate).

If the blood removal rate is in the blood removal condition range (S134: Yes), the process proceeds to a step in which a blood transfer rate (target blood transfer rate) is calculated based on the blood removal rate (S135). If the blood removal rate is not in the blood removal condition range (S134: No), the process proceeds to a step in which the out-of-condition blood removal display unit is turned on, and displays an out-of-condition blood removal state (S136).

(5) Subsequently, the blood transfer rate calculation unit 144 determines whether (blood removal rate>set upper limit blood removal rate) is satisfied by comparison of the blood removal rate calculated in S133 with the blood removal condition data (the set upper limit blood removal rate) (S137).

If (blood removal rate>set upper limit blood removal rate) is not satisfied (S137: No), the process proceeds to S135, and the linked control is performed. If (blood removal rate>set upper limit blood removal rate) is satisfied (S137: Yes), the process proceeds to a step in which an upper limit value of the blood transfer rate is set (S138), and a blood transfer rate is set in correspondence with the out-of-condition blood removal. If the upper limit value of the blood transfer rate is set, the process proceeds to S135.

(6) Subsequently, the roller pump control amount calculation unit 145 calculates a control amount (rotational speed) with reference to the blood transfer rate characteristic of the roller pump 120, based on the blood transfer rate calculated in S135 or the upper limit value of the blood transfer rate (blood transfer rate corresponding to the out-of-condition blood removal) set in S138 (S139).

(7) Subsequently, the roller pump control unit 146 outputs a signal to the roller pump 120 in correspondence with the control amount (S140).

S131 to S140 are repeatedly executed at predetermined intervals while the linked control of the artificial heart and lung apparatus 100 is performed.

Since the artificial heart and lung apparatus 100 of the first embodiment is capable of detecting the out-of-condition blood removal (blood removal rate<set lower limit blood removal rate, and blood removal rate>set upper limit blood removal rate), the artificial heart and lung apparatus 100 is capable of efficiently managing the out-of-condition blood removal.

According to the artificial heart and lung apparatus 100 of the first embodiment, if the out-of-condition blood removal is detected, the out-of-condition blood removal display unit 180 is turned on, and thus the control unit 140 is capable of efficiently ascertaining a change in blood removal rate.

If, when the blood transfer rate is controlled according to the blood removal rate, it is detected that the blood removal rate has exceeded the set upper limit blood removal rate, the artificial heart and lung apparatus 100 of the first embodiment performs control such that the blood transfer rate of the roller pump 120 becomes the upper limit value of the blood transfer rate or less. As a result, even if the blood removal rate changes and increases, it is possible to prevent an increase in blood pressure and blood transfer pressure, and to smoothly and stably perform surgery.

According to the artificial heart and lung apparatus 100 of the first embodiment, if an out-of-condition blood removal process for performing the out-of-condition blood removal has been performed, and then the out-of-condition blood removal is deactivated, the control of a blood transfer rate of the roller pump 120 automatically returns to the linked control. As a result, the artificial heart and lung apparatus 100 is capable of efficiently performing the linked control.

According to the artificial heart and lung apparatus 100 of the first embodiment, the control unit 140 controls a blood transfer rate of the roller pump 120 such that the blood transfer rate is linked with the blood removal rate, and synchronizes the blood transfer rate with the blood removal rate (or sets the blood transfer rate in the specific range). As a result, even if the blood removal rate changes, if is possible to stably circulate blood.

Since the artificial heart and lung apparatus 100 of the first embodiment includes the roller pump 120 as a blood transfer pump, the artificial heart and lung apparatus 100 is prevented from being affected by pressure, and is capable of transferring blood at a stable blood transfer rate.

According to the artificial heart and lung apparatus 100 of the first embodiment, the blood removal regulator 121 is provided in the blood removal line 101, and thus it is possible to suitably adjust a flow rate of blood to be removed via the blood removal line 101.

Second Embodiment

Hereinafter, an artificial heart and lung apparatus (blood circulation system) of a second embodiment of the present invention will be described with reference to FIGS. 6 to 9.

Figure 6:
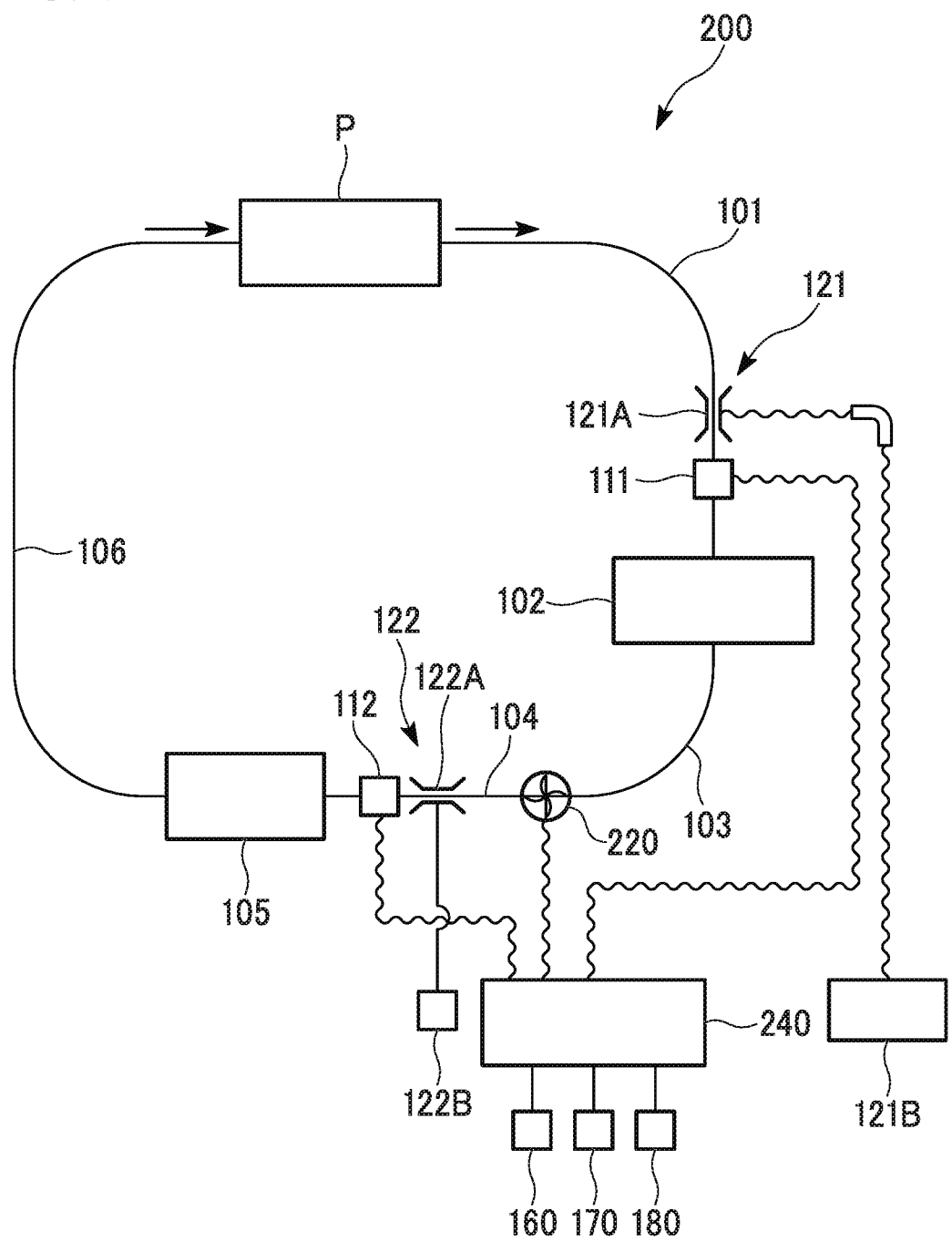
FIG. 6 is a circuit diagram showing a schematic configuration of an artificial heart and lung apparatus of a second embodiment of the present invention.
Figure 7:
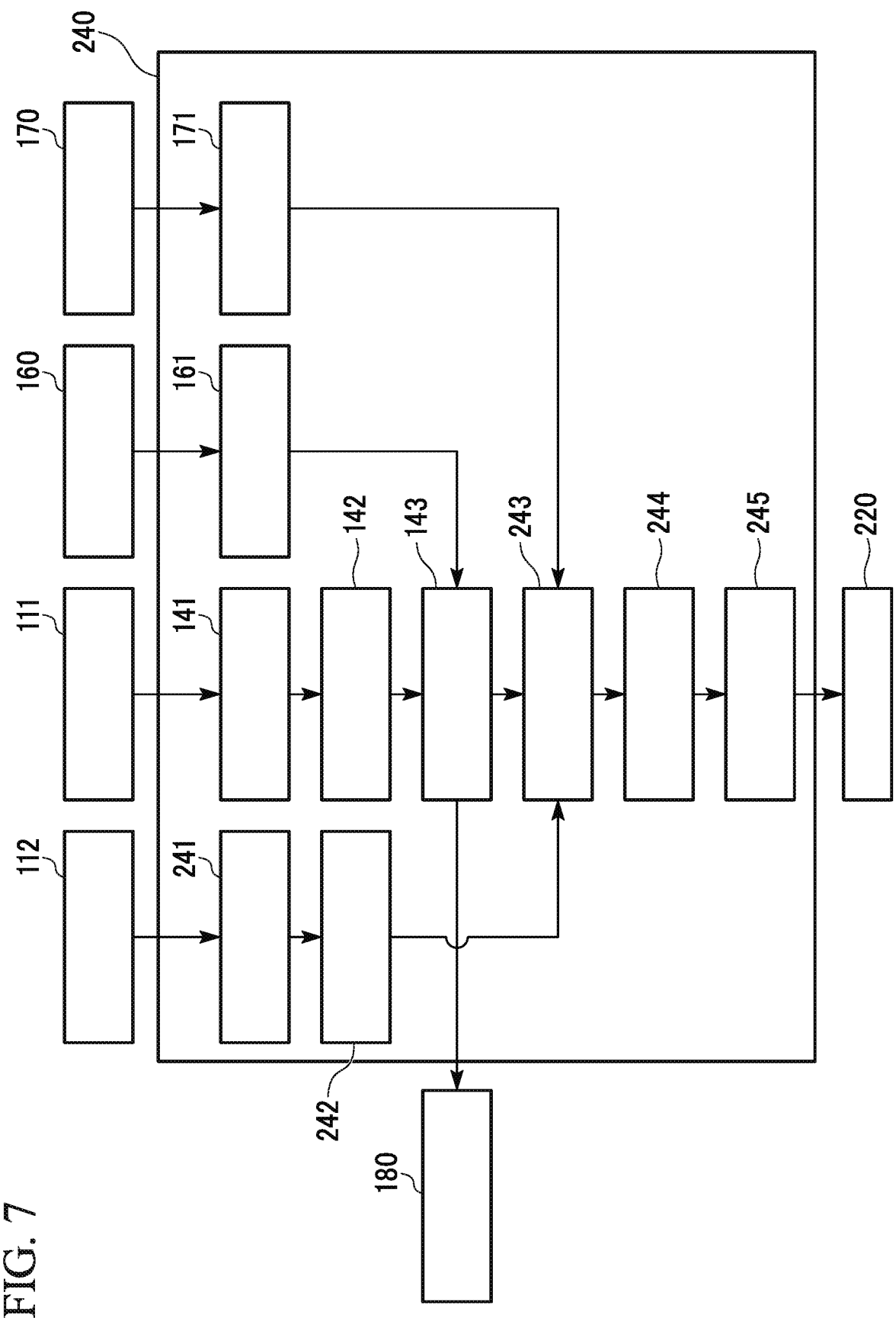
FIG. 7 is a block diagram showing a schematic configuration of a control unit of the artificial heart and lung apparatus of the second embodiment of the present invention.

FIG. 6 is diagram showing a schematic configuration of the artificial heart and lung apparatus of the second embodiment. FIG. 7 is a block diagram showing a schematic configuration of a control unit of the artificial heart and long apparatus of the second embodiment.

In FIGS. 6 and 7, reference sign 200 represents an artificial heart and lung apparatus, reference sign 111 represents a blood removal rate sensor (blood removal rate measurement means), reference sign 112 represents a blood transfer rate sensor (blood transfer rate measurement means), reference sign 220 represents a centrifugal pump (blood transfer pump), reference sign 240 represents a control unit, reference sign 160 represents a blood removal condition setting unit, reference sign 170 represents a blood transfer control switching unit, and reference sign 180 represents an out-of-condition blood removal display unit.

As shown in FIG. 6, the artificial heart and lung apparatus 200 includes the blood removal line 101; the reservoir 102; the blood line 103; the first blood transfer line (blood transfer line) 104; the artificial lung 105; the second blood transfer line (blood transfer line) 106; the blood removal rate sensor 111; a blood transfer rate sensor 112; the blood removal regulator (blood removal rate adjustment means) 121; a blood transfer regulator (blood transfer rate adjustment means) 122; a centrifugal pump (blood transfer pump) 220; a control unit 240; the blood removal condition setting unit 160; the blood transfer control switching unit 170; and the out-of-condition blood removal display unit 180.

In the embodiment, the artificial heart and long apparatus 200 is capable of performing the normal control in which a blood transfer rate of the centrifugal pump 220 is set independent of a blood removal rate, and the linked control in which the blood transfer rate is set according to the blood removal rate.

If out-of-set condition blood removal (representing a state in which a blood removal rate exceeds a set upper limit blood removal rate, or a state in which a blood removal rate is lower than a set lower limit blood removal rate, and hereinafter, referred to as out-of-condition blood removal) is performed in the normal control, the out-of-condition blood removal display unit 180 is turned on.

If out-of-condition blood removal is perforated in the linked control, the out-of-condition blood removal display unit 180 is turned on, and if a blood removal rate exceeds the set upper limit blood removal rate during the out-of-condition blood removal, blood is transferred at an upper limit value of the blood transfer rate.

The blood removal line 101, the reservoir 102, the blood line 103, the centrifugal pump 220, the first blood transfer line 104, the artificial lung 105, and the second blood transfer line 106 are connected together in the listed sequence.

The blood removal regulator 121 and the blood removal rate sensor 111 are disposed in the blood removal line 101 in the listed sequence.

The blood transfer regulator 122 and the blood transfer rate sensor 112 are disposed in the first blood transfer line 104 in the listed sequence.

The blood removal line 101, the reservoir 102, the blood line 103, the first blood transfer line 104, the artificial lung 105, the second blood transfer line 106, the blood removal rate sensor 111, the blood removal regulator 121, the blood removal condition setting unit 160, the blood transfer control switching unit 170, and the out-of-condition blood removal display unit 180 have the same as those of the first embodiment, and thus, a description thereof will be omitted here.

Similar to the blood removal rate sensor 111, an ultrasonic sensor is used as the blood transfer rate sensor (blood transfer rate measurement means) 112. The blood transfer rate sensor 112 sends a measurement result to the control unit 240.

The blood transfer rate measurement means includes not only measurement means for measuring a blood transfer rate, but also measurement means for measuring various blood removal rate parameters to specify a blood transfer rate.

Blood transfer rate parameters are parameters that change in correspondence with a blood transfer rate. The blood transfer rate parameters includes not only a blood transfer rate, but also various parameters to specify a blood transfer rate such as the flow speed of transferred blood in a case where a cross-sectional flow path area of the blood transfer line is already known, or a parameter (for example, a change in ultrasonic wave frequency) to specify the flow speed.

A comparison between a blood transfer rate parameter and a blood removal rate parameter implies any one of a comparison therebetween in a case where the types of the blood transfer rate parameter and the blood removal rate parameter are the same, a direct comparison therebetween in a case where the types of the blood transfer rate parameter and the blood removal rate parameter are different from each other, and a comparison therebetween after one of or both the blood transfer rate parameter and the blood removal rate parameter are converted into forms in which both can be compared to each other.

The centrifugal pump 220 suctions blood stored in the reservoir 102 via the blood line 103, and transfers the blood to the artificial lung 105 via the first blood transfer line 104 by rotating impeller blades via an AC servo motor or a DC servo motor.

The centrifugal pump 220 is controlled by a control signal output from the control unit 240. The rotational speed of the normal control is controlled independent of a blood removal rate. The rotational speed of the linked control is controlled such that a blood transfer rate measured by the blood transfer rate sensor 112 is synchronized with a blood removal rate measured by the blood removal rate sensor 111. The rotational speed is feedback controlled in either case.

The blood transfer regulator 122 is provided in the first blood transfer line 104. The blood transfer regulator 122 includes a clamper 122A formed of a pair of clamp members; a servo motor (not shown) that operates the clamper 122A; and a blood transfer regulator operation unit 122B. An operator blocks the first blood transfer line 104 by manually operating the blood transfer regulator operation unit 122B, and adjusting the amount of clamp (the amount of pinch) of the clamper 122A via the servo motor, and thus, the back flowing of blood when the centrifugal pump 220 stops is prevented. The first blood transfer line 104 may be blocked in linkage with the stopping of the centrifugal pump 220.

Hereinafter, a schematic configuration of the control unit 240 will be described with reference to FIG. 7. FIG. 7 is a block diagram showing the schematic configuration of the control unit 240 of the second embodiment.

The control unit 240 includes the blood removal rate signal input receiving unit 141; the blood removal rate calculation unit 142; an blood transfer rate signal receiving unit 241; a blood transfer rate calculation unit 242; a target blood transfer rate calculation unit 243; a centrifugal pump control amount calculation unit 244; a centrifugal pump control unit 245; the set blood removal condition data receiving unit 161; and the blood transfer control switching instruction receiving unit 171.

The control unit 240 is connected to the blood removal rate sensor 111, the blood transfer rate sensor 112, the blood removal condition setting unit 160, the blood transfer control switching unit 170, the out-of-condition blood removal display unit 180, and the centrifugal pump 220 via cables.

The blood removal rate signal input receiving unit 141, the blood removal rate calculation unit 142, the set blood removal condition data receiving unit 161, and the blood transfer control switching instruction receiving unit 171 are the same as those of the first embodiment, and thus a description thereof will be omitted here.

The blood transfer rate signal receiving unit 241 is connected to the blood transfer rate sensor 112, and receives a blood transfer rate signal (blood transfer rate parameter signal) sent from the blood transfer rate sensor 112.

The blood transfer rate calculation unit 242 calculates a blood transfer rate based on the blood transfer rate signal sent from the blood transfer rate signal receiving unit 241. Specifically, a blood transfer rate is calculated based on a flow path area of the first blood transfer line 104 and a blood transfer speed (flow rate parameter) calculated from the blood transfer rate signal.

The out-of-condition blood removal process unit 143 determines whether the blood removal rate is in a blood removal condition range, and detects out-of-condition blood removal, based on the blood removal rate received from the blood removal rate calculation unit 142 and the set blood removal condition data received from the set blood removal condition data receiving unit 161. If the out-of-condition blood removal is performed, the out-of-condition blood removal process unit 143 turns the out-of-condition blood removal display unit 180 on.

If the blood removal rate is in the blood removal condition range, and the blood removal rate of the out-of-condition blood removal does not exceed the set upper limit blood removal rate, that is, if (blood removal rate≤set upper limit blood removal rate) is satisfied, the out-of-condition blood removal process unit 143 sends the blood removal rate, which has been received from the blood removal rate calculation unit 142, to the target blood transfer rate calculation unit 243.

In contrast, if the out-of-condition blood removal is performed, and the blood removal rate exceeds the set upper limit blood removal rate, that is, if (blood removal rate>set upper limit blood removal rate) is satisfied, the out-of-condition blood removal process unit 143 sets and sends an upper limit value of the blood transfer rate to the target blood transfer rate calculation unit 243.

The set blood removal condition data is the same as that of the first embodiment, and thus a description thereof will be omitted here.

The blood transfer control switching unit 160 is capable of switching between the normal control and the linked control, and the target blood transfer rate calculation unit 243 calculates target blood transfer rates (blood transfer rate which is a target rate) of the centrifugal pump 220 in the normal control and the linked control.

The target blood transfer rate calculation unit 243 calculates a normal (is not the out-of-condition blood removal) target blood transfer rate of the normal control based on the amount of operation of a blood transfer rate adjustment latch (not shown) which is received via the out-of-condition blood removal process unit 143.

The target blood transfer rate calculation unit 243 calculates a normal (is not the out-of-condition blood removal) target blood transfer rate of the linked control based on the blood removal rate received via the out-of-condition blood removal process unit 143.

In the embodiment, the blood transfer rate is synchronized with the blood removal rate by making a blood transfer rate (target blood transfer rate) of the centrifugal pump 220 equal to the blood removal rate.

The synchronization of the blood transfer rate with the blood removal rate via the centrifugal pump 220 is one mode in which the blood transfer rate is controlled to be in a specific range (for example, in a range represented by a ratio of the blood transfer rate to the blood removal rate, or in a range represented by a flow rate difference between the blood transfer rate and the blood removal rate) of the blood removal rate.

The target blood transfer rate calculation unit 243 calculates blood transfer rates of the normal control and the linked control in a case where the out-of-condition blood removal is performed, based on blood transfer rate calculation data (in the embodiment, the upper limit value of the blood transfer rate) which has been received from the out-of-condition blood removal process unit 143 and corresponds to the out-of-condition blood removal.

The centrifugal pump control amount calculation unit 244 calculates a rotational speed (control amount) via feedback control by comparison of the target blood transfer rate sent from the target blood transfer rate calculation unit 243 with the blood transfer rate.

The control amount of the centrifugal pump 220 in the linked control is a control amount that synchronizes the blood transfer rate with the blood removal rate.

The centrifugal pump control unit 245 outputs a signal to the centrifugal pomp 220 in correspondence with the control amount received from the centrifugal pump control amount calculation unit 244.

<Switching Between Normal Control and Linked Control>

Switching between the normal control and the linked control is the same as that in the artificial heart and lung apparatus 100 of the first embodiment shown in FIG. 3, and thus a description thereof will be omitted here.

<Normal Control>

Figure 8:
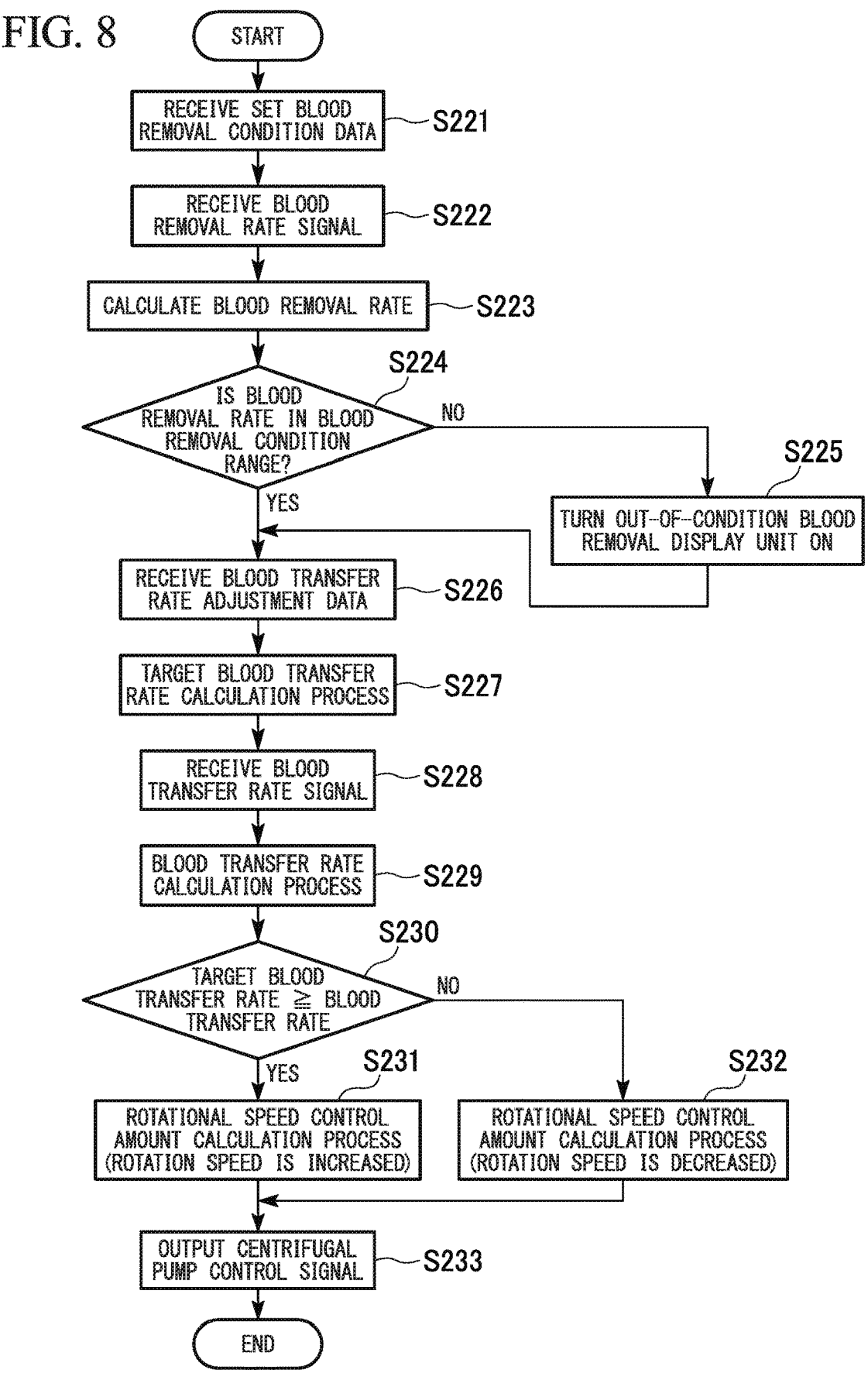
FIG. 8 is a flowchart showing an example of an operational sequence in normal control of the artificial heart and lung apparatus of the second embodiment of the present invention.

Hereinafter, an example of an operational sequence, in a case where the artificial heart and lung apparatus 200 of the second embodiment transfers blood in the normal control, will be described with reference to FIG. 8. FIG. 8 is a flowchart showing an example of an operational sequence of the normal control of the artificial heart and lung apparatus 200.

The operational sequence of the normal control of the artificial heart and lung apparatus 200 is as follows.

(1) First, the set blood removal condition data receiving unit 161 receives set blood removal condition data input from the blood removal condition setting unit 160 (S221).

(2) Subsequently, the blood removal rate signal input receiving unit 141 receives a blood removal rate signal (blood removal rate parameter signal) (S222).

(3) Subsequently, the blood removal rate calculation unit 142 calculates a blood removal rate based on the received blood removal rate signal (S223).

(4) Subsequently, the out-of-condition blood removal process unit 143 determines whether the blood removal rate is in the blood removal condition range by comparison of the blood removal rate calculated in S223 with the blood removal condition data (for example, the set upper limit blood removal rate and the set lower limit blood removal rate) (S224).

A determination as to whether the blood removal rate is in the blood removal condition range is made based on whether the blood removal rate satisfies (set upper limit blood removal rate≥blood removal rate≥set lower limit blood removal rate).

If the blood removal rate is not in the blood removal condition range (S224: No), the out-of-condition blood removal display unit is turned on, and the process proceeds to a step in which the out-of-condition blood removal display unit displays an out-of-condition blood removal state (S225). If the blood removal rate is in the blood removal condition range (S224: Yes), the process proceeds to a step in which the out-of-condition blood removal process unit 143 receives blood transfer rate adjustment data input from a blood transfer rate adjustment unit (not shown) (S226).

(5) Subsequently, the target blood transfer rate calculation unit 243 calculates a target blood transfer rate based on the received blood transfer rate adjustment data (S227).

(6) Subsequently, the blood transfer rate calculation unit 242 receives a blood transfer rate signal (S228).

(7) Subsequently, the blood transfer rate calculation unit 242 calculates a blood transfer rate based on the received blood transfer rate signal (S229).

(8) Subsequently, the centrifugal pump control amount calculation unit 244 calculates (target blood transfer rate−blood transfer rate), and determines whether (target blood transfer rate≥blood transfer rate) is satisfied by comparison of the target blood transfer rate calculated in S227 with the blood transfer rate calculated in S229 (S230).

If (target blood transfer rate≥blood transfer rate) is satisfied (S230: Yes), the process proceeds to a step in which the centrifugal pump control amount calculation unit 244 calculates a control amount (increased rotational speed) of the centrifugal pump 220 based on the difference (=(target blood transfer rate−blood transfer rate)) calculated in S230 (S231). If (target blood transfer rate≥blood transfer rate) is not satisfied (S230: No), the process proceeds to a step in which the centrifugal pump control amount calculation unit 244 calculates a control amount (decreased rotational speed) of the centrifugal pump 220 based on the difference (=(target blood transfer rate−blood transfer rate)) calculated in S230 (S232).

If the target blood transfer rate is equal to the blood transfer rate, the control amount (increased rotational speed) becomes zero.

(9) Subsequently, the centrifugal pump control unit 245 outputs a signal in correspondence with the control amount of the centrifugal pump 220 calculated in S231 or S232 (S233).

S221 to S233 are repeatedly executed at predetermined intervals while the normal control of the artificial heart and lung apparatus 200 is performed.

<Linked Control>

Figure 9:
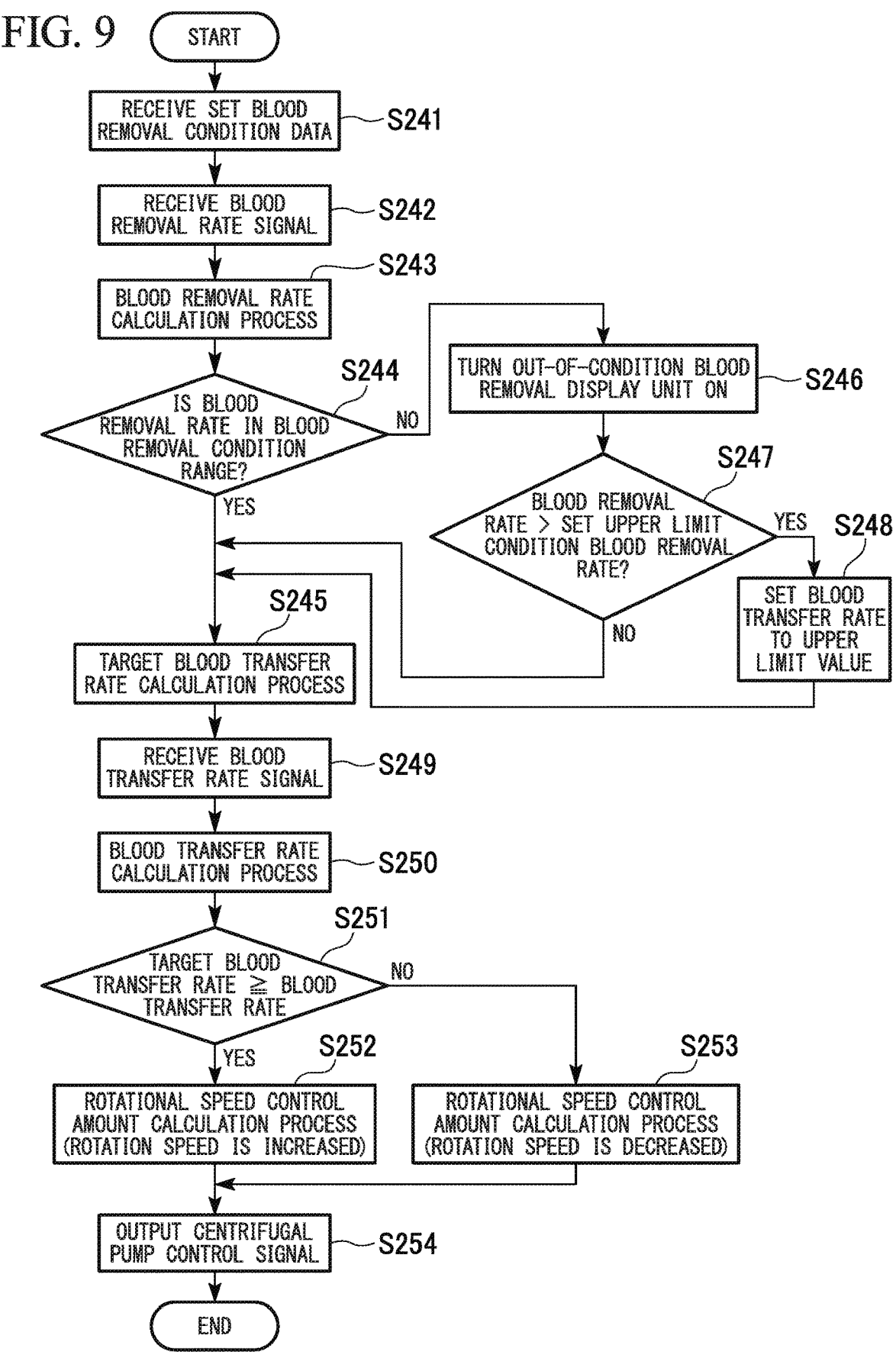
FIG. 9 is a flowchart showing an example of an operational sequence in linked control of the artificial heart and lung apparatus of the second embodiment of the present invention.
Figure 10:
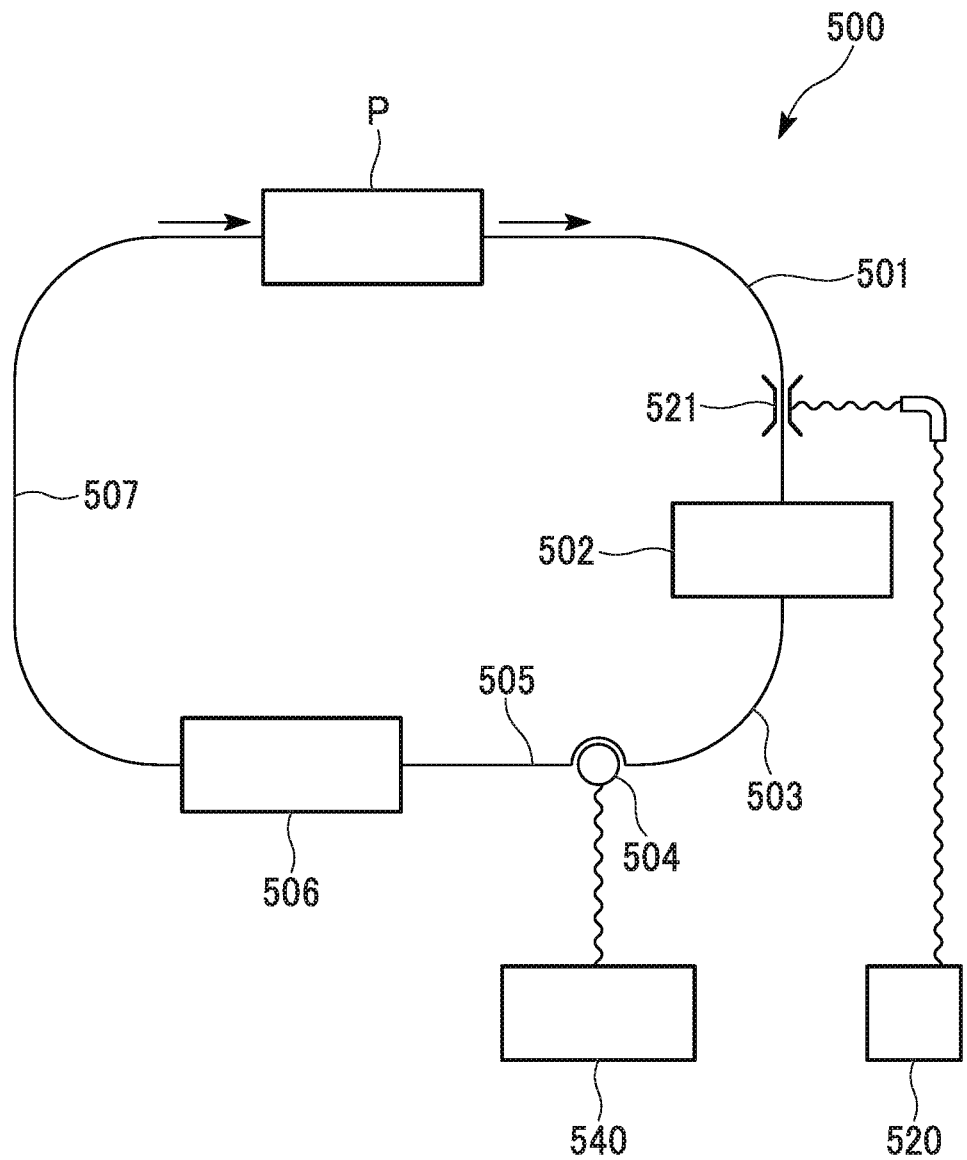
FIG. 10 is a diagram showing a schematic configuration of an artificial heart and lung apparatus in the related art.

Hereinafter, an example of an operational sequence of the linked control of the artificial heart and lung apparatus 200 will be described with reference to FIG. 9. FIG. 9 is a flowchart showing an example of an operational sequence of the linked control of the artificial heart and lung apparatus 200.

The operational sequence of the linked control of the artificial heart and lung apparatus 200 is as follows.

(1) First, the set blood removal condition data receiving unit 161 receives set blood removal condition data input from the blood removal condition setting unit 160 (S241).

(2) Subsequently, the blood removal rate signal input receiving unit 141 receives a blood removal rate signal (blood removal rate parameter signal) (S242).

(3) Subsequently, the blood removal rate calculation unit 142 calculates a blood removal rate based on the received blood removal rate signal (S243).

(4) Subsequently, the out-of-condition blood removal process unit 143 determines whether the blood removal rate is in the blood removal condition range by comparison of the blood removal rate calculated in S243 with the blood removal condition data (for example, the set upper limit blood removal rate and the set lower limit blood removal rate) (S244).

A determination as to whether the blood removal rate is in the blood removal condition range is made based on whether the blood removal rate satisfies (set upper limit blood removal rate≥blood removal rate≥set lower limit blood removal rate).

If the blood removal rate is in the blood removal condition range (S244: Yes), the process proceeds to a step in which a target blood transfer rate is calculated based on the blood removal rate (S245). If the blood removal rate is not in the blood removal condition range (S244: No), the process proceeds to a step in which the out-of-condition blood removal display unit is turned on, and displays an out-of-condition blood removal state (S246).

(5) Subsequently, the out-of-condition blood removal process unit 143 determines whether (blood removal rate>set upper limit blood removal rate) is satisfied by comparison of the blood removal rate calculated in S243 with the blood removal condition data (the set upper limit blood removal rate) (S247).

If (blood removal rate>set upper limit blood removal rate) is not satisfied (S247: No), the process proceeds to S245, and the linked control is performed. If (blood removal rate>set upper limit blood removal rate) is satisfied (S247: Yes), the process proceeds to a step in which an upper limit value of the blood transfer rate is set (S248), and a blood transfer rate is set in correspondence with the out-of-condition blood removal. If the upper limit value of the blood transfer rate is set, the process proceeds to S245.

(6) Subsequently, the blood transfer rate signal input unit 241 receives a blood transfer rate signal (blood transfer rate parameter signal) (S249).

(7) Subsequently, the blood transfer rate calculation unit 242 calculates a blood transfer rate based on the received blood transfer rate signal (S250).

(8) Subsequently, the centrifugal pump control amount calculation unit 244 calculates (target blood transfer rate−blood transfer rate) and determines whether (target blood transfer rate≥blood transfer rate) is satisfied by comparison of the target blood transfer rate calculated in S245 with the blood transfer rate calculated in S250 (S251).

If (target blood transfer rate≥blood transfer rate) is satisfied (S251: Yes), the process proceeds to a step in which a control amount (increased rotational speed) of the centrifugal pump 220 is calculated based on the difference (=(target blood transfer rate−blood transfer rate)) calculated in S251 (S252). If (target blood transfer rate≥blood transfer rate) is not satisfied (S251: No), the process proceeds to a step in which a control amount (decreased rotational speed) of the centrifugal pump 220 is calculated based on the difference (=(target blood transfer rate−blood transfer rate)) calculated in S251 (S253).

If the target blood transfer rate is equal to the blood transfer rate, the control amount (increased rotational speed) becomes zero.

(9) Subsequently, the centrifugal pump control unit 245 outputs a signal in correspondence with the control amount of the centrifugal pump 220 calculated in S252 or S253 (S254).

S241 to S254 are repeatedly executed at predetermined intervals while the linked control of the artificial heart and lung apparatus 200 is performed.

Since the artificial heart and lung apparatus 200 of the second embodiment is capable of detecting the out-of-condition blood removal (blood removal rate<set lower limit blood removal rate, and blood removal rate>set upper limit blood removal rate), the artificial heart and lung apparatus 200 is capable of efficiently managing the out-of-condition blood removal.

According to the artificial heart and lung apparatus 200 of the second embodiment, if the out-of-condition blood removal is detected, the out-of-condition blood removal display unit 180 is turned on, and thus the control unit 240 is capable of efficiently ascertaining a change in blood removal rate.

If, when the blood transfer rate is controlled according to the blood removal rate, it is detected that the blood removal rate has exceeded the set upper limit blood removal rate, the artificial heart and lung apparatus 200 of the second embodiment performs control such that the blood transfer rate of the centrifugal pump 220 becomes the upper limit value of the blood transfer rate or less. As a result, even if the blood removal rate changes and increases, it is possible to prevent an increase in blood pressure and blood transfer pressure, and to smoothly and stably perform surgery.

According to the artificial heart and lung apparatus 200 of the second embodiment, if an out-of-condition blood removal process for performing the out-of-condition blood removal has been performed, and then the out-of-condition blood removal is deactivated, the control of a blood transfer rate of the centrifugal pump 220 automatically returns to the linked control. As a result, the artificial heart and lung apparatus 200 is capable of efficiently performing the linked control.

In the artificial heart and lung apparatus 200 of the second embodiment, the centrifugal pump 220 is used as a blood transfer pump, and thus, it is possible to promptly transfer blood at a stable blood transfer rate.

In the artificial heart and lung apparatus 200 of the second embodiment, the blood removal regulator 121 is provided in the blood removal line 101, and thus, it is possible to suitably control the blood removal rate.

Since the blood transfer regulator 122 is provided in the first blood transfer line 104, it is possible to prevent the back flowing of blood by blocking the first blood transfer line 104 when the centrifugal pump 220 stops.

The present invention is not limited to the aforementioned embodiments, and changes can be made to the embodiments in various forms insofar as the changes do not depart from the concept of the invention.

The artificial heart and lung apparatuses 100 and 200 of the aforementioned embodiments synchronize the blood transfer rate with the blood removal rate. Alternatively, the blood transfer rate may be adjusted to be in a specific range of the blood removal rate.

In the aforementioned embodiments, the out-of-condition blood removal display unit 180 is used to alarm the out-of-set condition blood removal. Alternatively, a configuration element including an alarm may be used, or sound or voice alarm may be used.

In the aforementioned embodiments, an upper limit value of the blood transfer rate is set for a blood transfer rate of the roller pump 120 and the centrifugal pump 220. Alternatively, an upper limit value of the blood transfer rate may be controlled by the blood removal regulator 121 or the blood transfer regulator 122.

In the aforementioned embodiments, if (blood removal rate≤set upper limit blood removal rate) is satisfied after the blood transfer rate is calculated based on the upper limit value, an out-of-condition blood removal process is deactivated, and the control of the blood transfer rate automatically returns to the linked control. Alternatively, a configuration in which the control of the blood transfer rate does not automatically return to the linked control may be adopted, or the control of the blood transfer rate may automatically return to the linked control after a predetermined length of time has elapsed from when (blood removal rate≤set upper limit blood removal rate) has been satisfied. It is possible to arbitrarily set conditions for when the control of the blood transfer rate automatically returns to the linked control.

In the aforementioned embodiments, the set blood removal condition includes the set upper limit blood removal rate, the set lower limit blood removal rate, and the upper limit value of the blood transfer rate. In contrast, it is possible to arbitrarily set the configuration of the set blood removal condition.

In the first embodiment, the blood removal regulator 121 is provided, and in the second embodiment, the blood removal regulator 121 and the blood transfer regulator 122 are provided. Alternatively, a configuration in which neither the blood removal regulator 121 nor the blood transfer regulator 122 is provided may be adopted. A configuration in which either the blood removal regulator 121 or the blood transfer regulator 122 is provided may be adopted.

Flow rate adjustment means other than the blood removal regulator 121 and the blood transfer regulator 122 may be provided.

In the first and second embodiments, the blood removal regulator 121 and the blood removal rate sensor 111 are disposed in the blood removal line 101 in the listed sequence. Alternatively, the blood removal rate sensor 111 and the blood removal regulator 121 may be disposed in the listed sequence.

In the second embodiment, the blood transfer regulator 122 and the blood transfer rate sensor 112 are disposed in the first blood transfer line 104 in the listed sequence. Alternatively, the blood transfer rate sensor 112 and the blood transfer regulator 122 may be disposed in the listed sequence. The blood transfer regulator 122 and the blood transfer rate sensor 112 may be disposed in the second blood transfer line 106 instead of the first blood transfer line 104.

In the aforementioned embodiments, the blood removal rate sensor 111 and the blood transfer rate sensor 112 which measure the flow speed of blood are respectively used as blood removal rate measurement means and blood transfer rate measurement means. Alternatively, a blood removal rate and a blood transfer rate may be measured by measuring a blood removal rate parameter (including a blood removal rate) other than a blood removal speed, and a blood transfer rate parameter (including a blood transfer rate) other than a blood transfer speed.

In the aforementioned embodiments, ultrasonic sensors are used as the blood removal rate sensor 111 and the blood transfer rate sensor 112. Alternatively, various well-known flow rate measurement means using laser, infrared light, or the like may be used instead of an ultrasonic sensor.

In the aforementioned embodiments, the roller pump 120 and the centrifugal pump 220 are used as blood transfer pumps. Alternatively, other types of blood transfer pumps may be used.

In the first embodiment, the blood transfer rate sensor 112 is not provided in the blood transfer line. Alternatively, a flow rate sensor (flow rate parameter measurement means) such as an ultrasonic sensor may be suitably provided in the first blood transfer line 104 or the second blood transfer line 106.

In the aforementioned embodiments, examples of flowcharts are given to illustrate schematic steps of controlling the artificial heart and lung apparatuses 100 and 200. Alternatively, control may be performed via methods (algorithms) other than the methods shown in the flowcharts.

In the aforementioned embodiments, each of the artificial heart and lung apparatuses 100 and 200 includes the reservoir 102. Alternatively, an auxiliary circulation apparatus (blood circulation system) not including the reservoir 102 may be used.

INDUSTRIAL APPLICABILITY

According to the blood circulation system of the invention, it is possible to efficiently circulate blood so as to smoothly and stably proceed with surgery even if a blood removal rate changes.

REFERENCE SIGNS LIST

P: PATIENT (HUMAN BODY)
100, 200: ARTIFICIAL HEART AND LONG APPARATUS (BLOOD CIRCULATION SYSTEM)
101: BLOOD REMOVAL LINE
102: RESERVOIR
104: FIRST BLOOD TRANSFER LINE (BLOOD TRANSFER LINE)
105: ARTIFICIAL LUNG
106: SECOND BLOOD TRANSFER LINE (BLOOD TRANSFER LINE)
111: BLOOD REMOVAL RATE SENSOR (BLOOD REMOVAL RATE MEASUREMENT MEANS)
112: BLOOD TRANSFER RATE SENSOR (BLOOD TRANSFER RATE MEASUREMENT MEANS)
120: ROLLER PUMP (BLOOD TRANSFER PUMP)
121: BLOOD REMOVAL REGULATOR (BLOOD REMOVAL RATE ADJUSTMENT MEANS)
122: BLOOD TRANSFER REGULATOR (BLOOD TRANSFER RATE ADJUSTMENT MEANS)
140, 240: CONTROL UNIT
160: BLOOD REMOVAL CONDITION SETTING UNIT
180: OUT-OF-CONDITION BLOOD REMOVAL DISPLAY UNIT (ALARM)

220: CENTRIFUGAL PUMP (BLOOD TRANSFER PUMP)

The invention claimed is:

1. A blood circulation system that can be connected to a human body, and is configured to transfer removed blood to the human body via a blood transfer pump, the system comprising:

the blood transfer pump;

a blood removal line through which removed blood flows to the blood transfer pump;

a blood transfer line that is configured to transfer blood, which is sent from the blood transfer pump, to the human body;

a blood removal rate sensor that is provided in the blood removal line and measures a blood removal rate; and a control unit that controls a blood transfer rate of the blood transfer pump wherein the control unit includes a blood removal rate signal input receiving unit connected to the blood removal rate sensor and is configured to receive a blood removal rate parameter signal, and a set blood removal condition data receiving unit configured to receive a set upper limit blood removal rate and a set lower limit blood removal rate, wherein the control unit is configured to detect that the blood removal rate is greater than the set upper limit blood removal rate or is less than the set lower limit blood removal rate, and out-of-set condition blood removal is performed, and wherein the control unit is configured to perform linked control of the blood transfer pump in correspondence with the blood removal rate such that the blood transfer rate of the blood transfer pump is in a specific range of the blood removal rate measured by the blood removal rate sensor, wherein the set blood removal condition data receiving unit receives an upper limit value of the blood transfer rate, and wherein when the linked control is performed and when the blood removal rate is detected to exceed the set upper limit blood removal rate, the control unit performs control such that the blood transfer rate of the blood transfer pump is limited to the upper limit value of the blood transfer rate or less while being independent of the blood removal rate.

2. The blood circulation system according to claim 1, wherein, if the out-of-set condition blood removal is detected, the control unit outputs alarm.

3. The blood circulation system according to claim 1, wherein when the control unit controls the blood transfer rate of the blood transfer pump independent of the blood removal rate, and if the out-of-set condition blood removal is deactivated, the control unit returns blood transfer via the blood transfer pump to the linked control.

* * * * *